United States Patent
Weiper-Idelmann et al.

(10) Patent No.: US 6,245,945 B1
(45) Date of Patent: Jun. 12, 2001

(54) SELECTIVE HYDROLYSIS OF ACETALS OR KETALS IN THE PRESENCE OF PHTHALIDES

(75) Inventors: Andreas Weiper-Idelmann, Waldsee; Heinz Hannebaum, Ludwigshafen; Hermann Pütter, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/623,059

(22) PCT Filed: Feb. 13, 1999

(86) PCT No.: PCT/EP99/00954

§ 371 Date: Aug. 25, 2000

§ 102(e) Date: Aug. 25, 2000

(87) PCT Pub. No.: WO99/43640

PCT Pub. Date: Sep. 2, 1999

(30) Foreign Application Priority Data

Feb. 27, 1998 (DE) ............................................... 198 08 296

(51) Int. Cl.[7] .................................................. C07C 45/42

(52) U.S. Cl. ........................ 568/322; 568/309; 568/324; 568/426; 568/438

(58) Field of Search .................................... 568/315, 316, 568/322, 323, 426, 437, 309, 438

(56) References Cited

U.S. PATENT DOCUMENTS 5,206,442 * 4/1993 Mackenroth et al. ............... 568/447

* cited by examiner

Primary Examiner—Rosalynd Keys
(74) Attorney, Agent, or Firm—Oblon, Spivak, McClelland, Maier & Neustadt, P.C.

(57) ABSTRACT

A process for the selective hydrolysis of acetals in the presence of phthalides comprises reacting a mixture (M) comprising a) a phthalide of the formula (I)

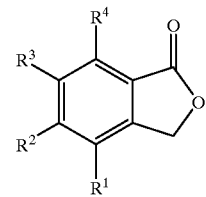

where:

$R^1, R^2, R^3$ and $R^4$: are independently hydrogen, $C_1$–$C_4$-alkyl or halogen, and b) an acetal or ketal of the formula (II)

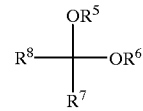

where:

$R^5$ and $R^6$: are independently $C_1$–$C_6$-alkyl, $C_6$–$C_{10}$-aryl or together ethylene, and $R^7$ and $R^8$: are independently $C_1$–$C_6$-alkyl, or one radical is a hydrogen and the other is a phenyl radical where from 1 to 3 hydrogen atoms of the phenyl radical may be replaced by $C_1$–$C_6$-alkyl radicals or $C_1$–$C_4$-alkoxy radicals, or $R^7$ and $R^8$ are together $C_3$–$C_6$-alkanediyl, and a hydrogen atom may be replaced by a hydroxyl group, at from 10 to 200° C. in the presence of from 1 to 10 mol of water, based on the amount of acetal or ketal of the formula (II), to hydrolyze the acetal or ketal of the formula (II) to the corresponding aldehyde or ketone.

11 Claims, No Drawings

SELECTIVE HYDROLYSIS OF ACETALS OR KETALS IN THE PRESENCE OF PHTHALIDES

This application is a 371 of PCT/EP99/00954, filed Feb. 13, 1999.

DESCRIPTION

The present invention relates to processes for selective hydrolysis of acetals and ketals in the presence of phthalides, which comprise reacting a mixture (M) comprising a) a phthalide of the formula (I)

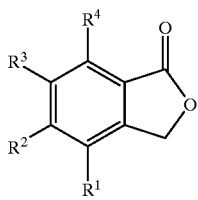

I where:

$R^1$, $R^2$, $R^3$ and $R^4$: are independently hydrogen, $C_1$–$C_4$-alkyl or halogen, and b) an acetal or ketal of the formula (II)

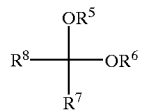

II where:

$R^5$ and $R^6$: are independently $C_1$–$C_6$-alkyl, $C_6$–$C_{10}$-aryl or together ethylene, and $R^7$ and $R^8$: are independently $C_1$–$C_6$-alkyl, or one radical is a hydrogen and the other is a phenyl radical where from 1 to 3 hydrogen atoms of the phenyl radical may be replaced by $C_1$–$C_6$-alkyl radicals or $C_1$–$C_4$-alkoxy radicals, or $R^7$ and $R^8$ are together $C_3$–$C_6$-alkanediyl, and a hydrogen atom may be replaced by a hydroxyl group, at from 10 to 200° C. in the presence of from 1 to 10 mol of water, based on the amount of acetal or ketal of the formula (II), to hydrolyze the acetal or ketal of the formula (II) to the corresponding aldehyde or ketone.

The present invention further relates to an overall process for preparing purified phthalides and aldehydes or ketones, of which the selective hydrolysis is an integral part and wherein a compound (III) selected from the group consisting of phthalic acid and phthalic acid derivatives of the general formula (III)

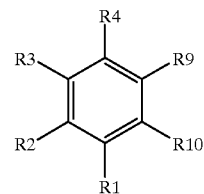

III where:

$R^1$, $R^2$, $R^3$ and $R^4$ are each as defined for the formula (I)

$R^9$ and $R^{10}$ are a) independently —COOH or COOX, where X is $C_1$–$C_4$-alkyl, b) either —COONY$_4$ while the other is CONH$_2$, Y is $C_1$–$C_4$-alkyl or hydrogen, c) together —CO—O—CO—, and from 0 to 20% by weight, based on the acetal or ketal of the formula (II), of a compound (IV) selected from the group consisting of methylbenzene, ring-substituted derivatives of methylbenzene where from 1 to 3 hydrogen atoms of the phenyl radical may be replaced by $C_1$–$C_6$-alkyl radicals or $C_1$–$C_4$-alkoxy radicals, cyclohexanone and 2-butanone are reacted electro-chemically in an undivided electrolysis cell to form a mixture (M), comprising phthalides of the formula (I) and aldehydes or ketones of the formula (II).

Phthalides of the formula (I) and aldehydes or ketones of the formula (II) (compounds I and II) are useful intermediates, especially for the synthesis of crop protection agents.

These compounds are preparable in a particularly economical way from the compounds (III) and (IV) in electrochemical cosyntheses in an undivided electrolysis cell, in which case the compounds (I) and (II) are obtained in the form of the mixture (M) (cf. DE-A-19618854 and the German application with the file reference 19741423.0).

However, separation of the resulting mixture (M) using technically simple customary separation processes such as distillation is very difficult, since the acetals/ketals and phthalides form azeotropes in some instances.

It is an object of the present invention to provide a technically simple and very economical separation process where the loss of product of value is minimal.

We have found that this object is achieved by the above-described process for separating the mixture (M) and the overall process for preparing the compounds (I) and (II).

The fact that the process of the present invention achieves the object must be surprising to those skilled in the art. First, it was unforeseeable that the aldehydes or ketones are significantly simpler to separate from the phthalides by distillation than the corresponding acetals or ketals. Secondly, the hydrolysis of acetals or ketals (II) in the presence of phthalides (I) would not have been expected to be economical.

The hydrolysis of acetals and ketals is described, for example, in J.Org.Chem. 59 (1994), 3098–3101. According to this reference, acetals and ketals are hydrolyzed in the presence of acids, acidic catalysts or auxiliaries, for example zeolites or ion exchangers, under harsh conditions in some instances, for example in super-critical water, in order that useful space-time yields may be obtained.

From this, it would have been expected that existing processes for hydrolyzing acetals or ketals of the formula (II) would not be economical under reaction conditions sufficiently mild to ensure that virtually only the acetal or ketal group and not the ester group of the phthalide is attacked, since the reaction times would be too long. On the other hand, harsher reaction conditions would be expected to cause the formation of by-products (hydrolysis of the phthalide).

The selective hydrolysis is particularly efficient in the case of those mixtures (M) comprising a phthalide of the formula (I) where $R^1$, $R^2$, $R^3$ and $R^4$ are all hydrogen.

Preference is given to acetals or ketals of the formula (II) wherein $R^7$ and $R^8$ have the following meanings:
one radical $R^7$ or $R^8$ is hydrogen and the other is selected from the group consisting of p-methoxyphenyl, p-methylphenyl, p-t-butylphenyl, o-methylphenyl and o-methoxyphenyl,
the radicals $R^7$ and $R^8$ are together 1-hydroxypentane-1, 5-diyl, or
one radical $R^7$ or $R^8$ is methyl and the other is 1-hydroxyethyl.

p-tert-Butylbenzaldehyde dimethyl acetal is particularly preferred.

The mixtures (M) comprise generally from 10 to 60%, preferably from 30 to 50%, by weight of a phthalide of the formula (I) and from 10 to 60 mol %, preferably from 30 to 50 mol %, of an acetal or ketal of the formula (II).

The mixtures (M) may further comprise from 0 to 20% by weight, based on the phthalide of the formula (I), of a compound (III) selected from the group consisting of phthalic acid and phthalic acid derivatives of the general formula (III)

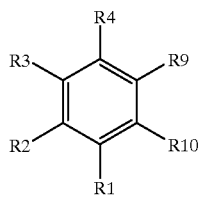

III where:
$R^1$, $R^2$, $R^3$ and $R^4$ are each as defined for the formula (I)
$R^9$ and $R^{10}$ are
a) independently —COOH or COOX, where X is $C_1$–$C_4$-alkyl,
b) either —COONY$_4$ while the other is CONH$_2$, Y is $C_1$–$C_4$-alkyl or hydrogen,
c) together —CO—O—CO—,
and from 0 to 20% by weight, based on the acetal or ketal of the formula (II), of a compound (IV) selected from the group consisting of methylbenzene, ring-substituted derivatives of methylbenzene where from 1 to 3 hydrogen atoms of the phenyl radical may be replaced by $C_1$–$C_6$-alkyl radicals or $C_1$–$C_4$-alkoxy radicals, cyclohexanone and 2-butanone.

In the mixtures (M), the radicals $R^1$ to $R^4$ in the compounds of the formulae (I) preferably have the same meanings as in the compounds of the formula (III).

The compounds of the formula (IV) are preferably compounds which serve as starting compounds for the electrochemical conversion to the corresponding compounds of the formula (I).

The selective hydrolysis is carried out in the presence of from 1 to 10 mol of water, based on the molar quantity of acetals or ketals of the formula (II). The reaction temperature is within the range from 10 to 200° C., preferably within the range from 80 to 140° C. The pressure at which the reaction is carried out is uncritical and is generally within the range from 0.5 to 10 bar.

The selective hydrolysis may be carried out in the presence of catalytic amounts of a mineral acid, of an organic acid or of an acidic ion exchanger, but preferably without the addition of catalyst.

The selective hydrolysis may be carried out in the presence of an inert organic solvent, for example acetone, or without a solvent.

The hydrolysis is preferably carried out according to one of the following variants:

Variant A:
The mixture (M) and the water are, via heat exchangers, separately preheated and fed into the reactor. The mixing can be influenced through internal fitments or stirrer optimization. Residence times are set to range from 10 sec to 10 min at a pressure of 3–20 bar and temperatures of 80–180° C. The reaction solution is expanded into a flash drum, the alcohol which is formed becoming substantially vaporized in the process.

Variant B:
Variant B1 of the present invention is a continuous hydrolysis under atmospheric pressure in a stirred reactor having a column fitted on top:

The mixture (M) and the water required for hydrolysis (stoichiometric amount up to 10-fold molar excess) are separately introduced into the vessel and reacted at from 100 to 140° C. in the course of a residence time of from 1 to 60 min. Surprisingly, sufficient water is still available in the reactor under these conditions to ensure complete hydrolysis of the starting material.

In a further embodiment (variant B2), the stream of mixture (M) is introduced via a column, ensuring intensive contact between the gaseous water ascending from the vessel and the stream of starting materials trickling down the column packing. This will in some cases permit a further reduction in the residence time in the stirred vessel and/or a better conversion.

The mixtures (M) are obtained, for example, by reacting a compound (III) electrochemically in an undivided electrolysis cell together with a compound (IV) in an organic solvent comprising less than 50% by weight of water by reacting a compound (III) electrochemically in an undivided electrolysis cell together with a compound (IV) in an organic solvent comprising less than 50% by weight of water.

The preparation of compounds of the formulae (I) and (II) from compounds (III) and (IV) in a coproduction by this process is described, for example, in DE-A-19618854 and 19741423.

In this process, the electrode materials used for both cathode and anode are in particular commercially available electrodes composed of graphite or carbon.

The electrolyte is customarily a from 2 to 40% strength by weight solution of a compound of the formula (III) in an organic solvent or in a mixture of an organic solvent and water, the mixture generally comprising less than 50% by weight, preferably less than 25% by weight, particularly preferably less than 5% by weight, of water.

Suitable organic solvents include in particular aliphatic $C_1$–$C_4$-alcohols, especially methanol or ethanol, or mixtures of such alcohols with a carboxamide such as dimethylformamide or t-butylformamide.

Examples of conducting salts present in the electrolytes are quaternary ammonium salts, such as tetra($C_1$–$C_4$-alkyl) ammonium halides or tetrafluoroborates and preferably methyltributyl-ammonium or methyltriethylammonium methosulfate, customarily in amounts of from 0.4 to 10% by weight, based on the electrolyte.

When aldehydes are prepared as coproducts, it is advisable to use $C_1$–$C_6$-alkyl alcohols or ethylene glycol as solvents, since the aldehydes become acetalized and protected from any further oxidation.

As regards the other process parameters such as temperature and current density, these are uncritical, as long as they are within the range customary for the electrochemical reaction of organic compounds. They are more particularly specified in DE-A-2510920, for example.

The electrolysis is generally carried on until the starting material of the formula (III) and/or the starting material of the formula (IV) has been virtually completely converted into the phthalide of the formula (I) or of the formula (II), respectively. In a preferred embodiment of the electrolysis, once the conversion is sufficient for the molar ratio (E), formed of the proportion of phthalide and the total of the proportion of phthalide and of phthalic acid and phthalic acid derivatives in the electrolyte, is within the range from 0.8:1 to 0.995:1, preferably within the range from 0.83:1 to 0.99:1, and particularly preferably within the range from 0.86:1 to 0.95:1, the electrolyte is discharged from the electrolysis cell.

One advantage of the last variant is that the proportion of undesirable by-products is particularly small and unconverted starting material, which essentially can only be removed in the course of the crystallization of the phthalide, as part of the mother liquor, can be put back into the electrolyte. The same is true of the coproduct and its starting compound, the anodic depolarizer. The process is therefore particularly economical.

The electrolysis may be carried out both batchwise and continuously.

In the continuous embodiment of the process, it is advantageous to harmonize the continuous discharge of the electrolyte and the continuous replenishment of the inert constituents of the electrolyte such as the solvents and conducting salts and also of the starting materials for the electrochemical reaction to one another and to the reaction rate in such a way that the concentration of all constituents of the electrolyte remains substantially constant. This applies especially to the molar ratio (E), which varies within the range defined.

In general, the discharged electrolyte is worked up by distillation prior to the selective hydrolysis. This distillative workup is preferably accomplished as follows:

Initially, the solvent is distilled out of the electrolyte, followed by a fraction comprising mixture (M). The remaining distillation residue mainly comprises the conducting salt, in general.

The distillation of the discharged electrolyte is generally carried out at a pressure of from 1 to 100 mbar and at a temperature of from 100 to 220° C. A thin-film evaporator, for example, is used. The distillation residue, which usually consists essentially of the conducting salt, can be returned into the electrolysis cell.

The electrolyte optionally prepurified in this way represents the mixture (M) and is subsequently subjected to the process of selective hydrolysis.

Following selective hydrolysis, the resulting reaction mixture, which comprises a phthalide of the formula (I) and the aldehyde or ketone freed from the acetal or ketal of the formula (II), is generally subjected to a fractional distillation.

The distillation is carried out according to customary methods. Preferably, at least 2 distinct fractions are collected. One of the fractions comprises essentially only the aldehyde or ketone. Further impurities are generally only present therein in amounts of up to 0.5% by weight.

A further fraction comprises a phthalide of the formula (I) as main constituent and, as the case may be, as further impurities, the compounds (III) and also the aldehyde. This fraction is particularly simple to purify further by crystallization when the proportion of these impurities is not more than 20%, preferably not more than 10%, by weight, based on the phthalide of the formula (I).

Advantageously, a third distinct fraction is recovered, mainly comprising low boilers. These are by-products having a lower boiling point than the products of value.

The crystallization process used for purifying the thus-recovered phthalide of the formula (I), hereinafter called "crude phthalide", is not subject to any restriction. The crystallization can be carried out continuously or batchwise, in one or more stages.

It is preferable in this context not to add an assistant, especially not to add an organic solvent.

The crystallization is preferably carried out in a single stage. In another preferred embodiment of the invention, the crystallization is carried out as a fractional crystallization.

In the art of fractional crystallization it is customary to term all stages which produce a crystallizate which is purer than the crude phthalide feed purifying stages and all other stages stripping stages. Multi-stage fractional crystallization processes are advantageously operated according to the counter-current principle whereby the crystallizate is separated from the mother liquor in each stage and fed to the particular stage having the next higher degree of purity, while the mother liquor is fed to the particular stage having the next lower degree of purity.

The temperature of the solution or melt during the crystallization is advantageously within the range from –10 to 75° C., especially within the range from 20 to 70° C. The solids content in the crystallizer is customarily within the range from 0 to 70 g, preferably within the range from 30 to 60 g, per 100 g of feed.

In a further advantageous embodiment of the invention, the crystallization takes place in apparatuses in which the crystals grow on cooled surfaces within the crystallization apparatus, i.e., are immobilized in the apparatus (e.g. layer crystallization process of Sulzer Chemtech (Switzerland) or static crystallization process of BEFS PROKEM (France).

Furthermore, the crystallization can be effected by cooling apparatus walls or by evaporating a solution of the crude phthalide under reduced pressure. Suitable for this purpose are in particular from 5 to 30% strength by weight solutions of the crude phthalide in methanol.

In the case of crystallization by cooling, the heat is removed via scraped-surface coolers connected to a stirred tank or to a vessel without stirrer. The circulation of the crystal suspension is ensured in this case by means of a pump. Alternatively, it is possible to remove the heat via the walls of a stirred tank having a close-clearance stirrer. A further preferred embodiment of cooling crystallization involves the use of cooling disc crystallizers as manufactured, for example by Gouda (Netherlands). In a further suitable variant for crystallization by cooling, the heat is removed via conventional heat transferors (preferably tube bundle or plate heat transferors). These apparatuses, unlike scraped-surface coolers, stirred tanks having close-clearance stirrers or cooling disc crystallizers, have no means for avoiding crystal layers on the heat-transferring surfaces. If, in operation, a state is reached where the heat transfer resistance has become too high owing to a crystal layer formation, the operation is switched over to a second apparatus. During operation of the second apparatus, the first apparatus is regenerated (preferably by melting of the crystal layer or by flushing the apparatus through with unsaturated solution). If heat transfer resistance becomes too high in the second apparatus, operation is switched back again to the first apparatus, etc. This variant can also be operated with more than two apparatuses in alternation. In addition, the crystallization can be effected by conventional evaporation of the solution under reduced pressure.

To separate the mother liquor from the crystallized-out phthalide, any known solid-liquid separation process is suitable. In a preferred embodiment of the invention, the crystals are separated from the mother liquor by filtration and/or centrifugation. Advantageously, the filtration or centrifugation is preceded by a (pre)thickening of the suspension, for example by means of one or more hydrocyclones. Centrifugation can be carried out in any known centrifuge which works batchwise or continuously. It is very advantageous to use pusher centrifuges which can be operated in one or more stages. Also suitable are screw sieve centrifuges or screw discharge centrifuges (decanters). A filtration is advantageously effected by means of press filters which can be operated batchwise or continuously, with or without stirrer, or by means of belt filters. In general, filtration can be effected under superatmospheric pressure or under reduced pressure.

The solid-liquid separation may be accompanied and/or followed by further process steps for increasing the purity of the crystals or of the crystal cake. In a particularly advantageous embodiment of the invention, the separation of the crystals from the mother liquor is followed by a single- or multiple-stage washing and/or sweating of the crystals or of the crystal cake.

In washing, the quantity of wash liquor is suitably within the range from 0 to 500 g of wash liquor/100 g of crystallizate, preferably within the range from 30 to 200 g of wash liquor/100 g of crystallizate.

Examples of suitable wash liquors are
a) the solvent, if the crystallization takes place in a solvent,
b) pure liquid product, or
c) liquid feed.

The washing can take place in apparatuses customary for the purpose. It is advantageous to use wash columns in which the removal of the mother liquor and the washing take place in one and the same apparatus, centrifuges which can be operated in one or more stages, or press filters or belt filters. The washing can be carried out on centrifuges or belt filters in one or more stages. The wash liquor can be passed in countercurrent to the crystal cake.

Sweating describes a local melting-off of impure regions. The sweat quantity is advantageously within the range from 0.1 to 90 g of molten-off crystallizate/100 g of crystallizate prior to sweating, preferably within the range from 5 to 35 g of molten-off crystallizate/100 g of crystallizate. It is particularly preferable to carry out the sweating on centrifuges or belt filters. A combined wash and sweat in one apparatus can also be suitable.

The purity of the phthalide obtained is preferably within the range from 97 to 99.9% by weight, especially within the range from 98.5 to 99.5% by weight.

The mother liquor and wash liquor can be returned into the electrolysis cell without further workup, especially if the crystallization was carried out without added assistant and the anodic coproduct was removed beforehand, since it consists essentially of a mixture of phthalide and the corresponding starting compound.

The same is true if the crystallization was carried out with the aid of solvents which are also used in the electrolyte.

If the crude phthalide was crystallized from a solution or washed with a solution which is not part of the electrolyte, the solvent is distilled off and the distillation residue can then be returned into the electrolysis cell.

As already mentioned in the introductory part of the description, the selective hydrolysis is an important step of an overall process for preparing high purity phthalides of the formula (I) together with the acetals in a particularly economical manner in an electrochemical coproduction process.

EXPERIMENTAL PART

Example 1

The starting 5642 g of p-t-butyltoluene (TBT) and 8681 g of dimethyl phthalate were reacted in an electrolysis similarly to Example 6 of DE-A-19618854, but without cosolvent and with N-methyl-N,N,N-tributylammonium methosulfate 1.2% by weight as conducting salt in 30 kg of MeOH.

After the reaction had ended (after consumption of a charge quantity of 4.5 F, based on TBT), the discharge was freed of solvent by distillation, and then the conducting salt and high boilers were removed via a short-path evaporator. The resulting crude product (12185 g) was hydrolyzed in a continuous stirred tank.

The crude product of the electrochemical cosynthesis had a p-tert-butylbenzaldehyde dimethyl acetal content of 33% and a phthalide content of 35%.

A portion of the crude product (1000 g) was introduced into a stirred tank having a column fitted on top, 62 g of water were added, and the mixture was heated to 106° C. Resulting methanol and the excess water distilled off through the column. The continuous feed of crude product and water into the stirred tank was then started, and a further 10,936 g of crude product were reacted in total. The level in the stirred tank was maintained via an overflow in such a way as to ensure a residence time of 30 min. The temperature was within the range from 102 to 110° C. The acetal conversion was $\geq 99.5\%$, and the crude aldehyde obtained (10,949 g) was 36% pure. 3744 g of pure p-tert-butylbenzaldehyde were recovered as main fraction from the hydrolysis discharge by rectification under reduced pressure. This corresponds to a yield of 61% of p-t-butylbenzaldehyde via the overall process. The selectivity is 83%, having regard to the recycling of the starting materials and intermediates.

The bottom 4780 g having a phthalide content of 71% were freed of high boilers via a short-path evaporator and subjected to a crystallization as described in Example 1 of DE-A-19741423. 3224 g of >99% of pure phthalide were obtained. This corresponds to a yield of 54% of phthalide via the overall process. The selectivity is 85%, having regard to the recycling of the starting materials and intermediates.

We claim:
1. A process for selective hydrolysis of acetals in the presence of phthalides, which comprises reacting a mixture (M) comprising a) a phthalide of the formula (I)

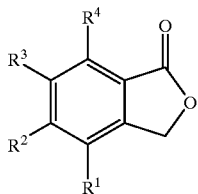

where:
$R^1, R^2, R^3$ and $R^4$: are independently hydrogen, $C_1$–$C_4$-alkyl or halogen, and b) an acetal or ketal of the formula (II)

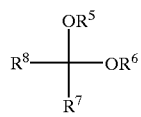

where:
$R^5$ and $R^6$: are independently $C_1$–$C_6$-alkyl, $C_6$–$C_{10}$-aryl or together ethylene, and $R^7$ and $R^8$: are independently $C_1$–$C_6$-alkyl, or one radical is a hydrogen and the other is a phenyl radical where from 1 to 3 hydrogen atoms of the phenyl radical may be replaced by $C_1$–$C_6$-alkyl radicals or $C_1$–$C_4$-alkoxy radicals, or $R^7$ and $R^8$ are together $C_3$–$C_6$-alkanediyl, and a hydrogen atom may be replaced by a hydroxyl group, at from 10 to 200° C. in the presence of from 1 to 10 mol of water, based on the amount of acetal or ketal of the formula (II), to hydrolyze the acetal or ketal of the formula (II) to the corresponding aldehyde or ketone.

2. A process as claimed in claim 1, wherein $R^7$ and $R^8$ have the following meanings:

one radical $R^7$ or $R^8$ is hydrogen and the other is selected from the group consisting of p-methoxyphenyl, p-methylphenyl, p-t-butylphenyl, o-methylphenyl and o-methoxyphenyl, the radicals $R^7$ and $R^8$ are together 1-hydroxypentane-1,5-diyl, or one radical $R^7$ or $R^8$ is methyl and the other is 1-hydroxyethyl.

3. A process as claimed in claim 1, wherein $R^1, R^2, R^3$ and $R^4$ in the formula (I) are all hydrogen.

4. A process as claimed in claim 3, wherein the phthalide of the formula (I) is a compound where $R^1, R^2, R^3$ and $R^4$ are hydrogen and the acetal of the formula (II) is p-tert-butyl-benzaldehyde dimethyl acetal.

5. A process as claimed in claim 1, wherein said mixture (M) comprises from 0 to 20% by weight, based on the phthalide of the formula (I), of a compound (III) selected from the group consisting of phthalic acid and phthalic acid derivatives of the general formula (III)

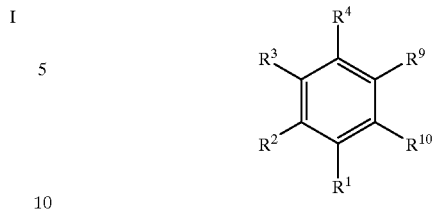

where:
$R^1, R^2, R^3$ and $R^4$ are each as defined for the formula (I)
$R^9$ and $R^{10}$ are
a) independently —COOH or COOX, where X is $C_1$–$C_4$-alkyl,
b) either —COONY$_4$ while the other is CONH$_2$, Y is $C_1$–$C_4$-alkyl or hydrogen,
c) together —CO—O—CO—, and from 0 to 20% by weight, based on the acetal or ketal of the formula (II), of a compound (IV) selected from the group consisting of methylbenzene, ring-substituted derivatives of methylbenzene where from 1 to 3 hydrogen atoms of the phenyl radical may be replaced by $C_1$–$C_6$-alkyl radicals or $C_1$–$C_4$-alkoxy radicals, cyclohexanone and 2-butanone.

6. A process as claimed in claim 1, wherein the reaction is carried out in the presence of catalytic amounts of a mineral acid, of an organic acid or of an acidic ion exchanger.

7. A process as claimed in claim 1, further comprising subjecting the reaction mixture to a fractional distillation following the selective hydrolysis.

8. A process as claimed in claim 1, wherein said mixture (M), comprising the phthalides of the formula (I) and the acetals or ketals of the formula (II), is prepared by electrolysis by reacting a compound (III) electrochemically in an undivided electrolysis cell together with a compound (IV) in an organic solvent comprising less than 50% by weight of water.

9. A process as claimed in claim 8, wherein, once the conversion in the electrolysis is sufficient for the molar ratio (E), formed of the proportion of phthalide and the total of the proportion of phthalide of the formula (I) and of compound (III) in the electrolyte, is within the range from 0.8:1 to 0.995:1, the electrolyte is discharged from the electrolysis cell and subjected to the process of selective hydrolysis and, following the fractional distillation of the reaction mixture, the phthalide of the formula (I) is crystallized out and optionally removed from the mother liquor.

10. A process as claimed in claim 8, wherein, following the electrolysis, the discharged electrolyte is worked up by distillation prior to the selective hydrolysis.

11. A process as claimed in claim 10, wherein the electrolyte is worked up by distilling the organic solvent and then a fraction comprising the phthalides of the formula (I) and the acetals or ketals of the formula (II) alongside one another from the electrolyte.

* * * * *